United States Patent
Lan et al.

(10) Patent No.: US 8,373,353 B2
(45) Date of Patent: Feb. 12, 2013

(54) ALTERNATING CURRENT LIGHT EMITTING DIODE DEVICE

(75) Inventors: Pei-Hsuan Lan, Banciao (TW); Jui-Hung Chen, Taoyuan (TW); Jen-Hua Yang, Luodong Township, Yilan County (TW); Yu-Bing Lan, Banciao (TW)

(73) Assignee: Forward Electronics Co., Ltd. (TW)

( * ) Notice: Subject to any disclaimer, the term of this patent is extended or adjusted under 35 U.S.C. 154(b) by 430 days.

(21) Appl. No.: 12/656,854

(22) Filed: Feb. 18, 2010

(65) Prior Publication Data

US 2010/0225233 A1  Sep. 9, 2010

(30) Foreign Application Priority Data

Mar. 5, 2009  (TW) ................................ 98203309 U

(51) Int. Cl.
*H05B 41/16*   (2006.01)

(52) U.S. Cl. ......................................... 315/250; 257/88

(58) Field of Classification Search .................... 257/88, 257/99, 536; 315/246, 250
See application file for complete search history.

(56) References Cited

U.S. PATENT DOCUMENTS

| | | | | |
|---|---|---|---|---|
| 7,714,348 B2 * | 5/2010 | Fan et al. | ........................ | 257/99 |
| 2009/0066208 A1 * | 3/2009 | Ng | ..................................... | 313/1 |
| 2009/0167202 A1 * | 7/2009 | Miskin et al. | ................. | 315/250 |
| 2010/0259188 A1 * | 10/2010 | Cheng et al. | .................. | 315/294 |
| 2010/0320903 A1 * | 12/2010 | Yu | ................................... | 315/32 |

* cited by examiner

*Primary Examiner* — Don Le

(74) *Attorney, Agent, or Firm* — Bacon & Thomas, PLLC

(57) ABSTRACT

An alternating current light emitting diode device is disclosed, which comprises a substrate having a supporting surface and two supporting elements locating on the two sides of the supporting surface; a plurality of LED grains set on the supporting surface; a first chip resistor set on one of the two supporting elements; and a plurality of electrical wires providing electrical connections between the LED grains, and between the LED grain and the first chip resistor. Therefore, the total wattage of the AC LED device can be lowered to a designed range by using a chip resistor with proper resistance, and the total illumination efficiency can be increased.

11 Claims, 3 Drawing Sheets

ALTERNATING CURRENT LIGHT EMITTING DIODE DEVICE

BACKGROUND OF THE INVENTION

1. Field of the Invention

The present invention relates to an alternating current light emitting diode (i.e. AC LED) device and, more particularly, to an alternating current light emitting diode device capable of lowering total luminescent wattage to a predominant range and increasing total luminescent efficiency.

2. Description of Related Art

With reference to FIG. 1, there is shown a conventional AC LED device, which comprises a substrate 11, a plurality of LED grains 121, 122, 123, 124, and a plurality of electrical wires 131, 132, 133, 134, 135. The substrate 11 has a supporting surface 111 and two supporting elements 112 and 113 respectively locating on the two sides of the supporting surface 111; the plurality of LED grains 121, 122, 123, 124 are set on the supporting surface 111. Each of the electrical wires 132, 133, 134 provides electrical connections between the LED grains 121, 122, 123, and 124; the electrical wire 131 electrically connects the LED grain 121 with the supporting element 112, and the electrical wire 135 electrically connects the LED grain 124 with the supporting element 113. Besides, a sealed portion (not shown) may be further contained in this conventional AC LED device; the sealed portion may be set on the substrate 11 and covers the substrate 11, the LED grains 121, 122, 123, 124, and the plurality of electrical wires 131, 132, 133, 134, 135.

According to the conventional AC LED device as shown in FIG. 1, the substrate 11 is an insulated substrate, and there are four LED grains 121, 122, 123, 124 that are all AC LED grains and connected in series (tandem connection) through those electrical wires 132, 133, 134.

The said sealed portion (not shown) can function as a lens and is made of a transparent sealant; the sealed portion comprises a plurality of lenses portion (not shown) located corresponsively to the LED grains 121, 122, 123, 124; those lenses portion are set for modulating light illuminated from the LED grains 121, 122, 123, 124.

Owing to the limitation of the conventional technique for fabricating LED grains, it is impossible to precisely control the distributing positions of the illuminating wattage of each of the LED grain. As a result, precisely controlling on the total illuminating wattage of the AC LED device comprising a plurality of AC LED grains still causes considerable difficulties to those skilled in this art. Besides, in the practical situation, the real total wattage of an AC LED device is often higher than the expected one.

In order to solve this problem, a method of utilizing resistors connecting at the outer portion of the AC LED device is used to lower the total wattage of an AC LED device to a designed range. However, the excess value of the total wattage for each AC LED device is not always the same. Therefore, testing of the illumination wattage of each of the AC LED grains is needed, for selecting a resistor having proper resistance during the manufacturing process of the conventional AC LED device. As a result, the manufacturing cost is increased, and the manufacturing processe becomes more complicated.

Therefore, it is desirable to provide an improved AC LED device that has the ability for lowering the total wattage to a designed range and can increase the total illumination efficiency.

SUMMARY OF THE INVENTION

The object of the present invention is to provide an alternating current light emitting diode (i.e. AC LED) device, which enables the total illumination wattage of the AC LED device to be reduced to a predominated range.

Another object of the present invention is to provide an alternating current light emitting diode device with improved illumination efficiency.

To achieve the objects, the AC LED device of the present invention comprises a substrate having a supporting surface and two supporting elements respectively locating on the two sides of the supporting surface; a plurality of LED grains set on the supporting surface; a first chip resistor set on one of the two supporting elements; and a plurality of electrical wires providing electrical connections among the LED grains, and between the LED grains and the first chip resistor.

Therefore, by selecting and utilizing a chip resistor with a proper resistance to connect with the LED grains, wherein the chip resistor is mounted on one of the supporting elements. The total illumination wattage of the AC LED device of the present invention can be distributed in a constant range and may not be influenced by the different qualities between batches of the LED grains. Thus, the problem (complexity) to set the corresponding driving circuit in the later processes can be solved (reduced) by employing the AC LED device of the present invention. Furthermore, there is no need to add a resistor connecting at the outer portion of the AC LED device for lowering the total wattage of the AC LED device, because the total wattage of the AC LED device of the present invention has been lowered to a predominated range previously. Therefore, the cost for applying the AC LED device of the present invention can be reduced and the processes for applying the AC LED device of the present invention may be simplified.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
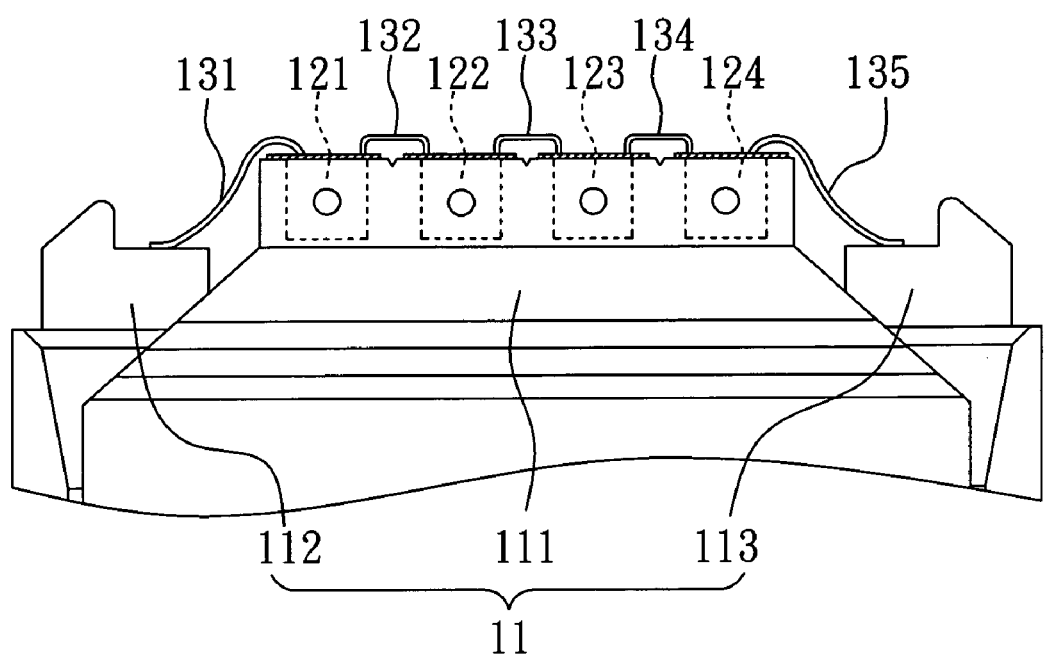
FIG. 1 is a schematic view of a conventional alternating current light emitting diode device.
Figure 2:
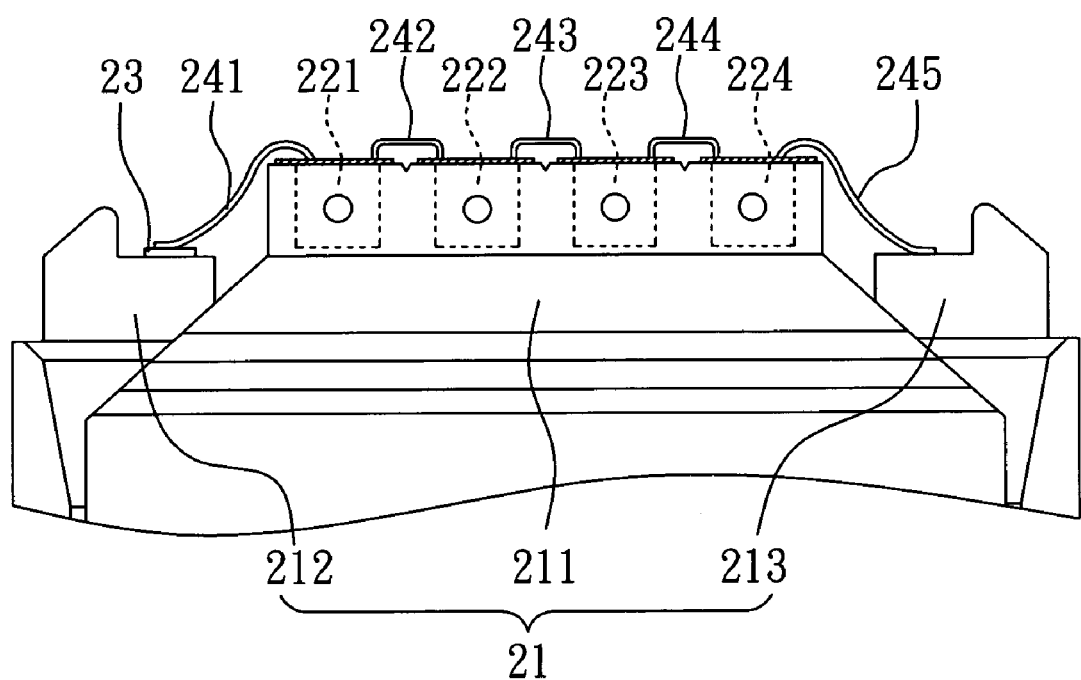
FIG. 2 is a schematic view of an alternating current light emitting diode according to one embodiment of the present invention.

With reference to FIG. 2, an alternating current light emitting diode device according to one embodiment of the present invention is shown, which comprises: a substrate 21, a plurality of LED grains 221, 222, 223, 224, a first chip resistor 23, and a plurality of electrical wires 241, 242, 243, 244, 245. The substrate 21 has a supporting surface 211 and two supporting elements 212, 213 respectively locating on the two sides of the supporting surface 211. The plurality of LED grains 221, 222, 223, 224 are set on the supporting surface 211. Besides, the first chip resistor 23 is set on one of the two supporting elements 212, 213. The electrical wires 242, 243, 244 are set among the plurality of LED grains 221, 222, 223, 224. The electrical wire 241 is set between the LED grain 221 and the first chip resistor 23, and the electrical wire 245 is set between the LED grain 224 and the supporting element 213.

Besides, the alternating current light emitting diode device according to one embodiment of the present invention may further comprise a sealed portion (not shown) set on the substrate 21 and covering the substrate 21, the LED grains 221, 222, 223, 224, the first chip resistor 23, and the electrical wires 241, 242, 243, 244, 245.

In the present embodiment, the substrate 21 is preferably an insulated substrate, and the LED grains 221, 222, 223, 224 are preferably AC LED grains. Besides, the total amount of the LED grains 221, 222, 223, 224 is four, wherein these LED grains 221, 222, 223, 224 are connected in series (by the electrical wires 242, 243, 244), and then together electrically connected with the first chip resistor 23.

In the present embodiment, the first chip resistor 23 is preferably a silicon chip resistor having a resistance of 400 ohm. The electrical wires 241, 242, 243, 244 are preferably gold wires. In addition, the sealed portion (not shown) may have a lensing function and may be made of a transparent sealant. That is, the sealed portion may comprise a plurality of lens portions (not shown) located corresponsively to the LED grains 221, 222, 223, 224, wherein these lens portions are set for modulating light illuminated from the LED grains 221, 222, 223, 224.

Therefore, after receiving the LED grains from the upstream provider, tests and records of the illuminating wattage for each of the LED grains by using a chip testing device is first proceeded. Subsequently, silicon chip resistors with proper resistances are selected according to the previously recorded values, and the selected silicon chip resistors are mounted on the supporting elements of the substrate. Thus, the ranges of the total wattage of the alternating current light emitting diode device of the present invention may be identical though the batches of the LED grains, which in prior art may have resulted in problems to set the corresponding driving circuit in the later processes. Furthermore, there is no need to add a resistor connecting at the outer portion of the alternating current light emitting diode device for lowering the total wattage of the alternating current light emitting diode device, because the total wattage of the alternating current light emitting diode device of the present invention has been lowered to a predominated range previously. Therefore, the cost for applying the alternating current light emitting diode device of the present invention can be reduced and the processes for applying the alternating current light emitting diode device of the present invention may be simplified.

For example, for manufacturing an alternating current light emitting diode device having a total illumination wattage of 5 W, as the individual value of the illumination wattage of each LED grain ranging between 1.7 W and 1.9 W, the value of total wattage of the alternating current light emitting diode device may exceed the designed value, i.e. 5 W (1.7 W×4=6.8 W>5 W), if no chip resistor is set on one of the two supporting elements. As a result, a heat dissipating device should be added to dissipate excess heat. Also, the plastic part of the conventional alternating current light emitting diode device will be easily embrittled due to the excess heat, thus the life span of the conventional alternating current light emitting diode device is expectably shortened.

Consequently, the total illumination wattage of the alternating current light emitting diode device can be reduced to the range of 5.2 W to 5.5 W, the illumination brightness can also reduce from 220 lm~240 lm (without silicon chip resistors) to 200 lm~220 lm (added with silicon chip resistors), after a 400 ohm silicon chip resistor being mounted on one of the two supporting elements of the alternating current light emitting diode device. Furthermore, the total illumination efficiency of the alternating current light emitting diode device is increased from 32.35 lm/W (without silicon chip resistors) to 38.46 lm/W (added with silicon chip resistors), which is apparently a great improvement.

Figure 3:
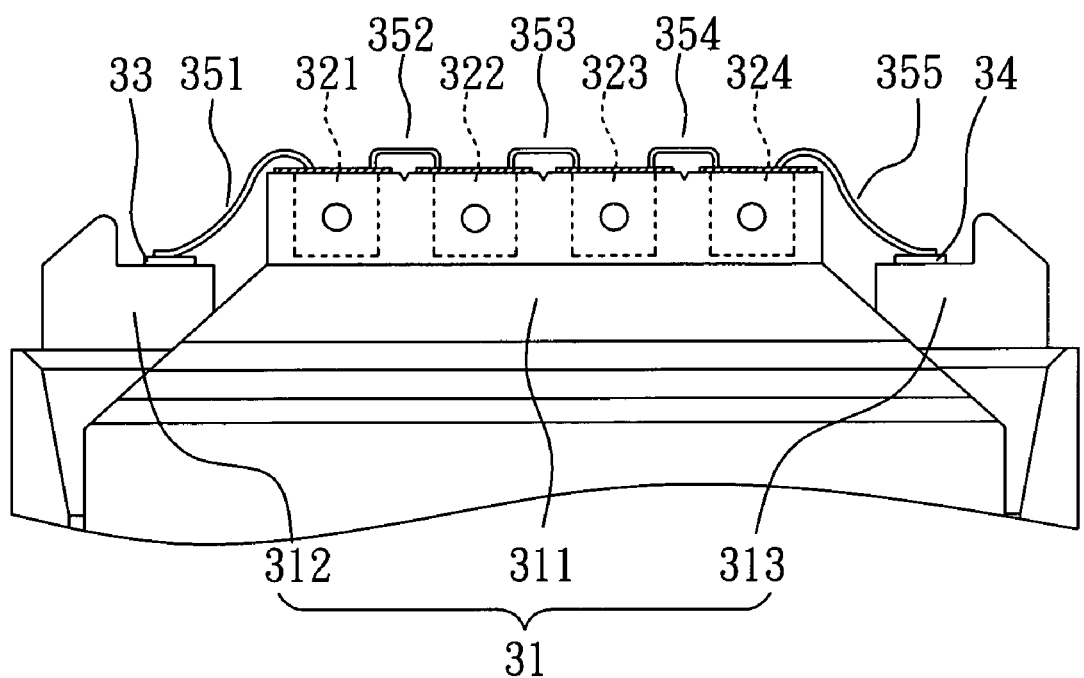
FIG. 3 is a schematic view of an alternating current light emitting diode according to one another embodiment of the present invention.

With reference to FIG. 3, an alternating current light emitting diode device according to one another embodiment of the present invention is shown, which comprises: a substrate 21, a plurality of LED grains 321, 322, 323, 324, a first chip resistor 33, a second chip resistor 34, and a plurality of electrical wires 351, 352, 353, 354, 355. The substrate 31 has a supporting surface 311 and two supporting elements 312, 313 respectively locating on the two sides of the supporting surface 311. The plurality of LED grains 321, 322, 323, 324 is set on the supporting surface 311. Besides, the first chip resistor 33 is set on the supporting element 312, and the second chip resistor 34 is set on the supporting element 313. The electrical wires 352, 353, 354 are set among the plurality of LED grains 321, 322, 323, 324. The electrical wire 351 is set between the LED grain 321 and the first chip resistor 33, and the electrical wire 355 is set between the LED grain 324 and the second chip resistor 34.

Besides, the alternating current light emitting diode device according to one another embodiment of the present invention may further comprise a sealed portion (not shown) set on the substrate 31 and covering the substrate 31, the LED grains 321, 322, 323, 324, the first chip resistor 33, the second chip resistor 34, and the electrical wires 351, 352, 353, 354, 355.

In the present embodiment, the substrate 31 is preferably an insulated substrate, and the LED grains 321, 322, 323, 324 are preferably AC LED grains. Besides, the total amount of the LED grains 321, 322, 323, 324 is four, wherein these LED grains 321, 322, 323, 324 are connected in series (by the electrical wires 352, 353, 354) and then together electrically connected with the first and second chip resistors 33, 34.

In the present embodiment, the first chip resistor 33 is preferably a silicon chip resistor having a resistance of 200 ohm, and also the second chip resistor 34 is preferably a silicon chip resistor having a resistance of 200 ohm. The resistances of the first and second chip resistors 33, 34 may be different from each other or the same, and are not specially limited. For example, the resistance of the first chip resistor 33 may be 100 ohm while the resistance of the second chip resistor 34 may be 300 ohm, and the efficiency (i.e. the total reducing wattage) of the alternating current light emitting device is the same as that of the alternating current light emitting including two silicon chip resistors having the same 200 ohm resistance.

Furthermore, the electrical wires 351, 352, 353, 354, 355 of the present embodiment are gold wires. The sealed portion (not shown) may have a lensing function and may be made of a transparent sealant. That is, the sealed portion may comprise a plurality of lens portions (not shown) located corresponsively to the LED grains 321, 322, 323, 324, wherein these lens portions are set for modulating light illuminated from the LED grains 321, 322, 323, 324.

As mentioned above, by selecting and utilizing a chip resistors with proper resistance to connect with the LED grains (wherein these chip resistors are mounted on the supporting elements respectively), the total illumination wattage of the AC LED device of the present invention can be distributed in a constant range and may not be influenced by the different qualities between batches of the LED grains. Thus, the problem (complexity) to set the corresponding driving circuit in the later processes can be solved (reduced) when the AC LED device of the present invention are used. Furthermore, there is no need to add a resistor connecting at the outer portion of the AC LED device for lowering the total wattage of the AC LED device, because the total wattage of the AC LED device has been lowered to a predominated range previously. Therefore, the cost for applying the AC LED device of the present invention can be reduced and the processes for applying the AC LED device of the present invention may be simplified.

Although the present invention has been explained in relation to its preferred embodiment, it is to be understood that many other possible modifications and variations can be made without departing from the scope of the invention as hereinafter claimed.

What is claimed is:

1. An alternating current light emitting diode device comprising:
    a substrate having a supporting surface and two supporting elements respectively locating on the two sides of the supporting surface;
    a plurality of LED grains set on the supporting surface;
    a first chip resistor set on one of the two supporting elements,
    a plurality of electrical wires providing electrical connections among the LED grains, and between the LED grains and the first chip resistor; and
    wherein the substrate is an insulated substrate.

2. The alternating current light emitting diode device as claimed in claim 1, further comprising a sealed portion set on the substrate and covering the substrate, the LED grains, the first chip resistor, and the electrical wires.

3. The alternating current light emitting diode device as claimed in claim 1, wherein the LED grains are alternating current light emitting diode grains.

4. The alternating current light emitting diode device as claimed in claim 1, wherein the LED grains are connected in series, and together connected with the first chip resistor.

5. The alternating current light emitting diode device as claimed in claim 1, wherein the alternating current light emitting diode device includes four LED grains.

6. The alternating current light emitting diode device as claimed in claim 1, wherein the first chip resistor is a silicon chip resistor.

7. The alternating current light emitting diode device as claimed in claim 1, wherein the electrical wires are gold wires.

8. The alternating current light emitting diode device as claimed in claim 1, further comprising a second chip resistor, wherein the first and second chip resistors are separately set at different supporting elements.

9. The alternating current light emitting diode device as claimed in claim 8, wherein the second chip resistor is a silicon chip resistor.

10. The alternating current light emitting diode device as claimed in claim 8, wherein the LED grains are connected in series, and the two LED grains located at two ends of the series connect with the first and second chip resistors separately.

11. The alternating current light emitting diode device as claimed in claim 2, wherein the sealed portion having a lensing function is made of a transparent sealant.

* * * * *